US010475710B1

United States Patent
Guo et al.

(10) Patent No.: US 10,475,710 B1
(45) Date of Patent: Nov. 12, 2019

(54) METHOD OF CHARACTERIZING THE ANISOTROPIC, COMPLEX DIELECTRIC CONSTANT FOR MATERIALS WITH SMALL DIMENSIONS

(71) Applicant: UCHICAGO ARGONNE, LLC, Chicago, IL (US)

(72) Inventors: Peijun Guo, Woodridge, IL (US); Richard D. Schaller, Clarendon Hills, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 16/035,330

(22) Filed: Jul. 13, 2018

(51) Int. Cl.
*H01L 21/66* (2006.01)
*G01N 21/41* (2006.01)
*H01L 21/324* (2006.01)
*H01L 21/02* (2006.01)

(52) U.S. Cl.
CPC ............ *H01L 22/12* (2013.01); *G01N 21/41* (2013.01); *H01L 21/02636* (2013.01); *H01L 21/324* (2013.01)

(58) Field of Classification Search
None
See application file for complete search history.

(56) References Cited

U.S. PATENT DOCUMENTS 5,073,026 A * 12/1991 Isobe ..................... G01N 21/41
356/369

5,414,506 A 5/1995 Saisho et al.
2009/0239314 A1* 9/2009 Haberjahn ............. H01L 22/12
438/8

OTHER PUBLICATIONS

Ghamsari, B. "Measuring the Complex Optical Conductivity of Graphene by Fabry-Perot Reflectance Spectroscopy" Sci. Rep. 6, Sep. 29, 2016 pp. 1-6 (Year: 2016).*
Alias, M. "Optical constants of CH3NH3PbBr3 perovskite thin films measured by spectroscopic ellipsometry" opt. Express vol. 24, No. 15, Jul. 25, 2016 pp. 16586-16594 (Year: 2016).*
Abdelwahab, et al., "Highly Enhanced Third-Harmonic Generation in 2D Perovskites at Excitonic Resonances," ACS Nano 12(1), pp. 644-650 (2018).
Atwater & Polman, "Plasmonics for improved photovoltaic devices," Nature Materials 9, pp. 205-213 (2010).
Back, et al., "Realization of an Electrically Tunable Narrow-Bandwidth Atomically Thin Mirror Using Monolayer MoSe2," Physical Review Letters 120:037401 (2018).
Blancon, et al,. "Extremely efficient internal exciton dissociation through edge states in layered 2D perovskites," Science, 10 pages (2017).
Booker, et al., "Formation of Long-Lived Color Centers for Broadband Visible Light Emission in Low-Dimensional Layered Perovskites," Journal of the American Chemical Society 139(51), pp. 18632-18639 (2017).

(Continued)

*Primary Examiner* — Grant S Withers
(74) *Attorney, Agent, or Firm* — Foley & Lardner LLP

(57) ABSTRACT

A dielectric-coating based technique determines the refractive index of small dimension materials. The technique utilizes a sample of the small dimension material coated with the dielectric and an uncoated sample, where reflectivity is determined for each. The real and imaginary components of the refractive index can be determined for the small-dimension material itself.

19 Claims, 12 Drawing Sheets

(56) References Cited

OTHER PUBLICATIONS

Buchholz, et al., "Differences between amorphous indium oxide thin films," Progress in Natural Science: Materials International 23(5), pp. 475-780 (2013).
Caldwell, et al,. "Sub-diffractional volume-confined polaritons in the natural hyperbolic material hexagonal boron nitride," Nature Communications 5:5221, 9 pages (2014).
Caldwell, et al., "Atomic-scale photonic hybrids for mid-infrared and terahertz nanophotonics," Nature Nanotechnology 11, pp. 9-15 (2016).
Dai, et al., "Graphene on hexagonal boron nitride as a tunable hyperbolic metamaterial," Nature Nanotechnology 10, pp. 682-686 (2015).
Dresselhaus, "Solid State Physics Part II: Optical Properties of Solids," Massachusetts Institute of Technology, 198 pages.
Evmenenko, et al., "Morphological Evolution of Multilayer Ni/NiO Thin Film Electrodes during Lithiation," ACS Applied Materials & Interfaces 8(31), pp. 19979-19986 (2016).
Ginzburg, et al., "Manipulating polarization of light with ultrathin epsilon-near-zero metamaterials," Optics Express 21(12), pp. 14907-14917 (2013).
Graf, et al., "Near-infrared exciton-polaritons in strongly coupled single-walled carbon nanotube microcavities," Nature Communications 7:13078, 7 pages (2016).
Guo, et al., "Electron-Phonon Scattering in Atomically Thin 2D Perovskites," ACS Nano 10(11), pp. 9992-9998 (2016).
Hu, et al., "Probing optical anisotropy of nanometer-thin van der waals microcrystals by near-field imaging," Nature Communications 8:1471, 8 pages (2017).
Ithurria, et al., "Colloidal nanoplatelets with two-dimensional electronic structure," Nature Materials 10, pp. 936-941 (2011).
Jariwala, et al., "Van der Waals Materials for Atomically-Thin Photovoltaics: Promise and Outlook," ACS Photonics 4(12), pp. 2962-2970 (2017).
Kats, et al., "Nanometre optical coatings based on strong interference effects in highly absorbing media," Nature Materials 12, pp. 20-24 (2013).
Krishnamoorthy, et al., "Topological Transitions in Metamaterials," Science 336(6078), pp. 205-209 (2012).
Leguy, et al., "Experimental and theoretical optical properties of methylammonium lead halide perovskites," Nanoscale 9, pp. 6317-6327 (2016).
Lin, et al., "Influences of evaporation temperature on electronic structures and electrical properties of molybdenum oxide in organic light emitting devices," Journal of Applied Physics 107:053703 (2010).
Maculan, et al., "CH3NH3PbCl3 Single Crystals: Inverse Temperature Crystallization and Visible-Blind UV-Photodetector," Journal of Physical Chemistry Letters 6(19), pp. 3781-3786 (2015).
Maier, "Plasmonics: Fundamentals and Applications," Springer Science & Business Media, 224 pages (2007).
Mak, et al., "Atomically Thin MoS2: A New Direct-Gap Semiconductor," Physical Review Letters 105:136805, 15 pages (2010).
Mao, et al., "Role of Organic Counterion in Lead- and Tin-Based Two-Dimensional Semiconducting Iodide Perovskites and Application in Planar Solar Cells," Chemistry of Materials 28(21), pp. 7781-7792 (2016).
Nadkarni & Simmons, "Electrical Properties of Evaporated Molybdenum Oxide Films," Journal of Applied Physics 41:545, (1970).

Naik, et al., "Titanium nitride as a plasmonic material for visible and near-infrared wavelengths," Optical Materials Express 2(4) pp. 478-489 (2012).
Najafov, et al., "Observation of long-range exciton diffusion in highly ordered organic semiconductors," Nature Materials 9, pp. 938-943 (2010).
Narimanov, et al., "Reduced reflection from roughened hyperbolic metamaterial," Optics Express 21(12), pp. 1456-14961 (2013).
O'Brien, et al., "Single-crystal-to-single-crystal intercalation of a low-bandgap superatomic crystal," Nature Chemistry 9, pp. 1170-1174 (2017).
Pazos-Outon, et al., "Photon recycling in lead iodide perovskite solar cells," Science 351(6280), pp. 1430-1433 (2016).
Poddubny, et al., "Hyperbolic metamaterials," Nature Photonics 7, pp. 948-957 (2013).
Saidaminov, et al., "High-quality bulk hybrid perovskite single crystals within minutes by inverse temperature crystallization," Nature Communications 6:7586, 6 pages (2015).
Saidaminov, et al., "Low-Dimensional-Networked Metal Halide Perovskites: The Next Big Thing," ACS Energy Letters 2(4), pp. 889-896 (2017).
Scuri, et al., "Large Excitonic Reflectivity of Monolayer MoSe2 Encapsulated in Hexagonal Boron Nitride," Physical Review Letters 120:037402, 6 pages (2018).
Shekhar, et al., "Hyperbolic metamaterials: fundamentals and applications," Nano Convergence 1:14, 17 pages (2014).
Smith, et al., "Decreasing the electronic confinement in layered perovskites through intercalation," Chemical Science 8, pp. 1960-1968 (2017).
Sreekanth, et al., "Extreme sensitivity biosensing platform based on hyperbolic metamaterials," Nature Materials 15, pp. 621-627 (2016).
Stoumpos, et al., "Ruddlesden-Popper Hybrid Lead Iodide Perovskite 2D Homologous Semiconductors," Chemistry of Materials 28(8), pp. 2852-2867 (2016).
Tongay, et al., "Monolayer behaviour in bulk ReS2 due to electronic and vibrational decoupling," Nature Communications 5:3252, 6 pages (2014).
Tsai, et al., "High-efficiency two-dimensional Ruddlesden-Popper perovskite solar cells," Nature 536, pp. 312-316 (2016).
Tsakmakidis, et al., "Ultraslow waves on the nanoscale," Science 358(6361), 11 pages (2017).
Wright, et al., "Electron-phonon coupling in hybrid lead halide perovskites," Nature Communications 7:11755, 9 pages (2016).
Yaffe, et al., "Excitons in ultrathin organic-inorganic perovskite crystals," Physical Review B 92(4):045414, 7 pages (2015).
Yangui, et al., "Rapid and robust spatiotemporal dynamics of the first-order phase transition in crystals of the organic-inorganic perovskite (C12H25NH3)2PbI4," Scientific Reports 5:16634, 10 pages (2015).
Yu, et al., "Light Propagation with Phase Discontinuities: Generalized Laws of Reflection and Refraction," Science 334(6054), pp. 333-337 (2011).
Zhang, et al., "Centimeter-Sized Inorganic Lead Halide Perovskite CsPbBr3 Crystals Grown by an Improved Solution Method," Crystal Growth & Design 17(12), pp. 6426-6431 (2017).
Zhang, et al., "Reflectance study of the oscillator strength of excitons in semiconductor quantum wells," Physical Review B 50(11) (1994).
Zhu, et al., "Lead halide perovskite nanowire lasers with low lasing thresholds and high quality factors," Nature Materials 14, pp. 636-642 (2015).

\* cited by examiner

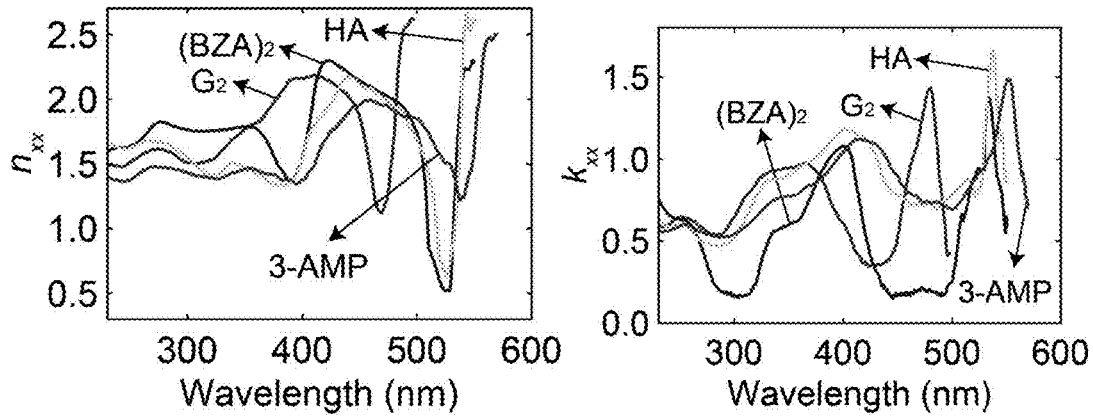
Fig. 3A
Fig. 3B
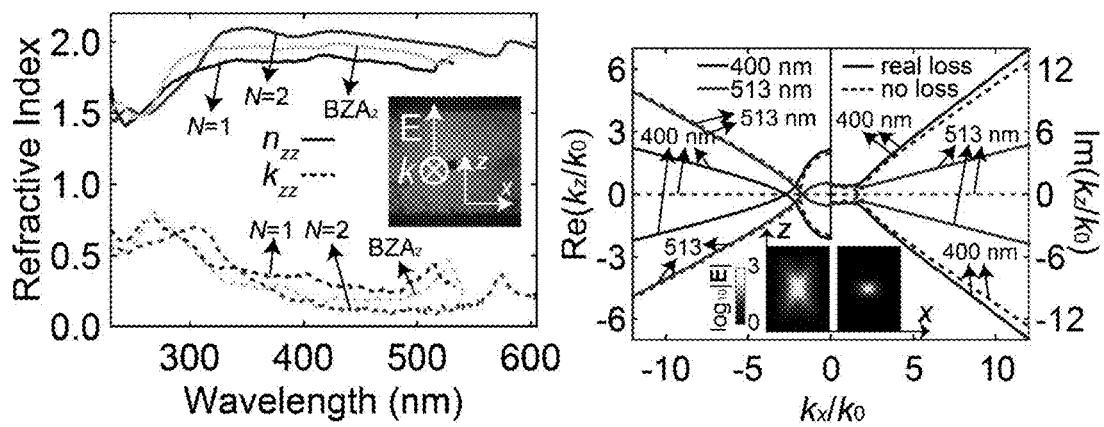
Fig. 3C
Fig. 3D
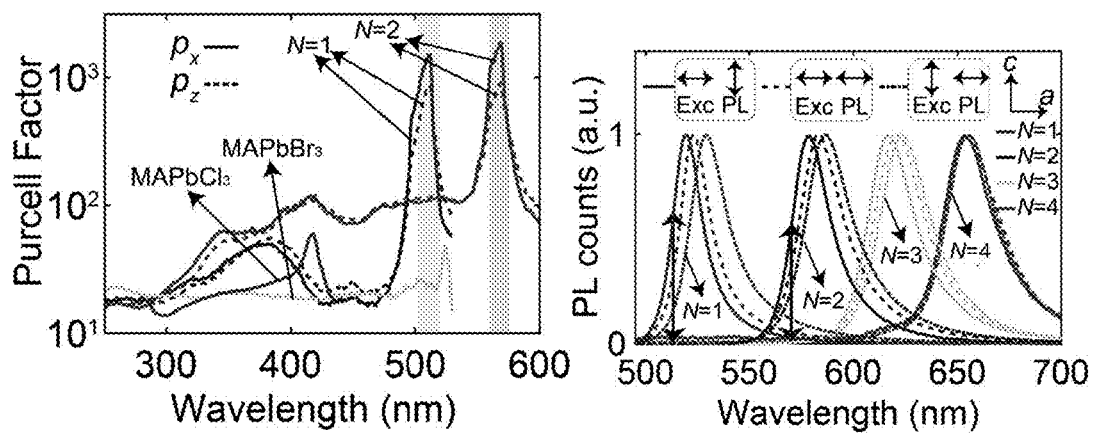
Fig. 3E
Fig. 3F

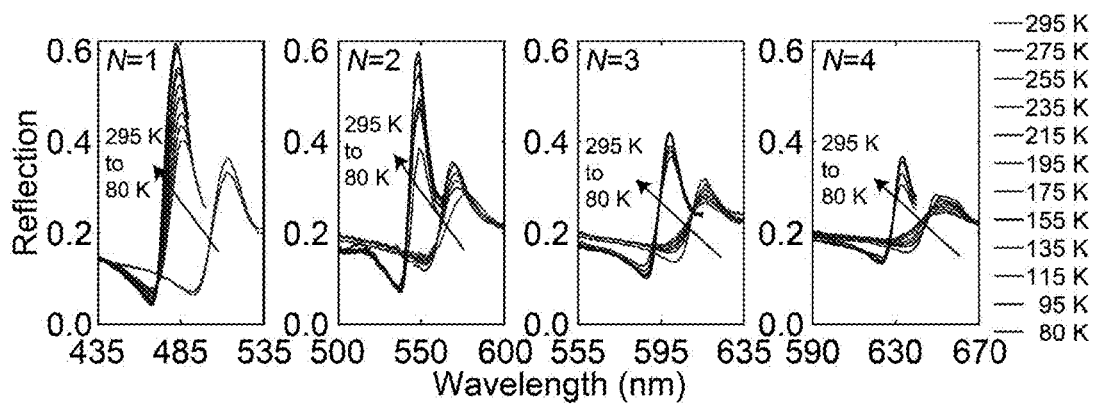
Fig. 4A
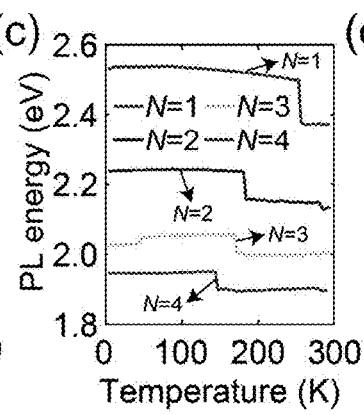
Fig. 4B
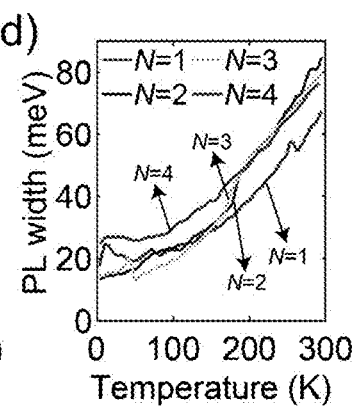
Fig. 4C
Fig. 4D
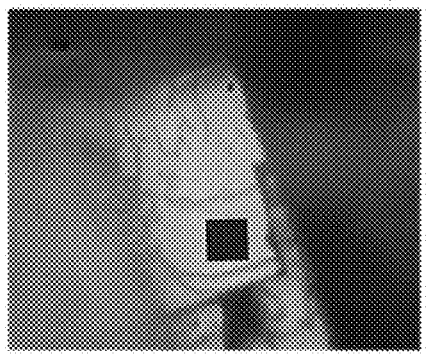
Fig. 5A
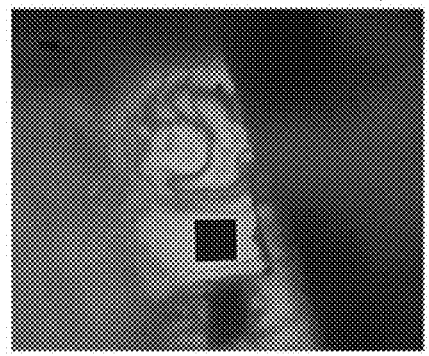
Fig. 5B (BZA)₂PbI₄

3AMP-PbI₄

HAPbI₄

G₂PbI₄

METHOD OF CHARACTERIZING THE ANISOTROPIC, COMPLEX DIELECTRIC CONSTANT FOR MATERIALS WITH SMALL DIMENSIONS

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates generally to systems and method of characterizing the dielectric constants for small-dimension materials (i.e., materials with small sizes).

BACKGROUND

Excitons are bound electron-hole pairs that represent one kind of elementary electronic excitations in materials with screened Coulomb interactions. Excitons, in similarity to plasmons (collective oscillations of free electrons) and phonons (collective lattice vibrations), can strongly couple with electromagnetic waves in the form of polaritons. At optical frequencies, the interaction between matter and electromagnetic waves is encoded into the relative permittivity ($\varepsilon$). Extensive studies on surface plasmon- and phonon-polaritons relied on $\varepsilon$ values that are near or below zero, which is essential for the confinement of light at sub-wavelength scales, and enabled numerous applications ranging from solar energy harvesting to ultrasensitive biosensing. Such regimes of $\varepsilon$ arising from excitons, however, have been much less explored, due to 1) a limited number of materials exhibiting strong excitonic effects and 2) the difficulty of extracting the values of $\varepsilon$ due to a lack of large-size materials typically needed for ellipsometry measurements. The recently re-emerged 2DHPs show extreme and tunable quantum-confinement effects and share the same layered structure as both artificially grown metal-dielectric superlattices and van der Waals materials such as h-BN. Development of a technique for characterizing the anisotropic permittivity, or, equivalently, the refractive index of 2DHPs and other small-sized materials is urgently needed. Understanding the similarity between excitons and other fundamental excitations, and their effect on $\varepsilon$ is crucial for improved nanophotonic and optoelectronic applications utilizing 2DHPs and other quantum-well-like materials.

SUMMARY

Embodiments described herein relate generally to a method of determining refractive index of a two-dimensional organic-inorganic hybrid perovskite. The method includes selecting a dielectric material with a known refractive index; depositing a coating of the dielectric material on a first sample of the two-dimensional organic-inorganic hybrid perovskite, the coating having a thickness; engaging the dielectric coated two-dimensional organic-inorganic hybrid perovskite with a laser of an optical testing device, the laser having a wavelength and the coating thickness being no more than ¼ of the wavelength; determining the reflectivity of the coated two-dimensional organic-inorganic hybrid perovskite; determining n and k of the refractive index of the coated two-dimensional organic-inorganic hybrid perovskite; determining the reflectivity of an uncoated sample of the two-dimensional organic-inorganic hybrid perovskite; determining a change in reflectivity ($\Delta R$) by comparing the reflectivity of the coated two-dimensional organic-inorganic hybrid perovskite and the reflectivity of the uncoated sample of the two-dimensional organic-inorganic hybrid perovskite; and determining the refractive index of the uncoated two-dimensional organic-inorganic hybrid perovskite at the wavelength based upon $\Delta R$ and the reflectivity of the uncoated sample of the two-dimensional organic-inorganic hybrid perovskite.

Other embodiments relate to a method of determining refractive index of a small dimension material. The method comprises: selecting a dielectric material with a known refractive index; depositing a coating of the dielectric material on a first sample of small-dimension material; engaging the dielectric coated small-dimension material with a laser of an optical testing device, the laser having a wavelength and the coating thickness being no more than ¼ of the wavelength; determining the reflectivity of the coated small-dimension material; determining the reflectivity of the uncoated small-dimension material; determining a change in reflectivity ($\Delta R$) by comparing the reflectivity of the coated small-dimension material and the reflectivity of the uncoated small-dimension material; and determining the refractive index of the uncoated small-dimension material at the wavelength based upon $\Delta R$ and the reflectivity of the uncoated small-dimension material.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 1A shows a schematic of the crystal structures of N=1 (left, 3D view) and N=2 (right, 2D view) 2DHP members, as well as the definition of the crystal axes. FIG. 1B shows optical micrographs of an N=3 single crystal flake before (top panel) and after (bottom panel) coating with MoOx, viewed along $\vec{c}$. The reflectivity spectrum was acquired from the region indicated by the black square. The white scalebar is 40 μm. FIG. 1C shows the calculated reflectivity of an infinitely thick absorbing medium with different n and k values; here n and k denote the real and imaginary parts of the refractive index, respectively. FIG. 1D shows the calculated change of reflectivity as a function of n and k of an absorbing medium, due to an 11 nm thick coating of $MoO_x$. Both FIG. 1C and FIG. 1D show results for normal incidence. FIG. 1D was obtained by subtracting data in FIG. 1C from data in FIG. 7B. FIG. 1E shows n and k of the evaporated $MoO_x$ layer deduced from ellipsometric measurements (shown in FIG. 6A-B). FIG. 1F shows X-ray reflectivity (left panel) data and fitted electron density (right panel) of the evaporated $MoO_x$ layer on Si and GaAs substrates.

FIG. 2A shows reflectivity from the ab-plane of single crystals of N=1~4. FIG. 2B shows the change of reflectivity after the coating with 11 nm of $MoO_x$. FIG. 2C shows the n values along the in-plane direction (ab-plane) for N=1-4 (only the above-bandgap regions are determined and shown). FIG. 2D shows the k values for N=1-4 (only the above-bandgap regions are determined and shown). FIG. 2E shows the $\epsilon'$ and $\epsilon''$ values for N=1~2. The shaded areas highlight the spectral regions where $\epsilon'<0$. FIG. 2F shows the a values (denoting the absorption coefficient) for N=1~4.

FIGS. 3A-F show the effects of organic spacers on the in-plane optical properties of 2DHPs, and the anisotropic optical properties of 2DHPs. FIG. 3A shows the n values for 2DHPs comprising of perovskite monolayers separated by different organic spacers. FIG. 3B shows the k values for 2DHPs comprising of perovskite monolayers separated by different organic spacers. FIG. 3C shows the n and k values along the c axis for N=1~2 and $(BZA)_2PbI_4$. FIG. 3D shows the iso-frequency curves for N=1 at 513 nm and 400 nm with real loss (solid lines) and no loss (dashed lines). The inset of FIG. 3D shows simulated electric field amplitude produced by a dipole polarized along $\vec{x}$ (left: 513 nm; right: 400 nm) with real loss. Width and height of the plotted domain are 50 nm and 75 nm, respectively. FIG. 3E shows simulated Purcell factors for 2DHPs (N=1~2), and three-dimensional (3D) perovskites ($MAPbBr_3$ and $MAPbCl_3$). FIG. 3F shows polarization resolved photoluminescence (PL) spectra for N=1, N=2, N=3 and N=4 (with excitation light normally incident onto the ac-plane. Polarizations of the excitation and collected PL were either parallel to $\vec{a}$ or $\vec{c}$ (inset). Double-sided black arrows indicate the center of the hyperbolic regimes for N=1~2.

FIGS. 4A-D show optical properties of 2DHPs at low temperatures. FIG. 4A shows temperature dependent reflectivity measured from the ab-plane of N=1~4. FIG. 4B shows temperature dependent PL spectra for N=4. FIG. 4C shows PL center energy. FIG. 4D shows PL full-width-half-maximum as a function of temperature for N=1~4.

FIG. 5A is an optical microscopic image of a pristine N=3 flake. FIG. 5B shows the same location after the sputtering of ~10 nm $Al_2O_3$. Surface damage is evident from the dramatic color change above the black square.

FIG. 1D in was obtained by subtracting data in FIG. 1C from data in FIG. 7B.

FIG. 12A shows $(BZA)_2PbI_4$, FIG. 12B shows $3AMP-PbI_4$, FIG. 12C shows $HAPbI_4$, and FIG. 12D shows $G_2PbI_4$.

FIG. 14A shows $\epsilon'$; FIG. 14B shows $\epsilon''$; FIG. 14C shows α; FIG. 14D shows n and k.

FIG. 15A shows reflectivity spectra (before and after $MoO_x$ coating) for N=1~2 and $(BZA)_2PbI_4$ from the ac-plane with light propagating along $\vec{b}$ and polarized along $\vec{c}$. FIG. 15B shows FIG. 15C shows $\epsilon''$, and FIG. 15D shows α for N=1, N=2 and $(BZA)_2PbI_4$. Data shown in FIGS. 15B-D are all for the out-of-plane (z) direction.

Figure 1A:
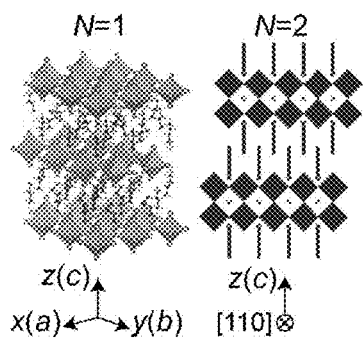
FIGS. 1A-F show characterization methodology of the indices of refraction for 2DHPs.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Knowledge of the refractive index is of crucial importance for the design of any optoelectronic and photonic devices including lenses, mirrors, photovoltaic cells, and light emitting diodes and lasers. Embodiments described herein relate generally to systems and methods for determining refractive index for materials with small dimensions. In particular, some embodiments provide method for determining refractive index for optically absorbing materials with dimensions below 50 microns, ultimately down to a couple times the optical wavelength of interest.

As used herein, small dimension materials mean solid-state materials including but not limited to single crystals, thin films, or nanoparticles, that have an optically flat and smooth surface, whose lateral dimension is on the order of or larger than several wavelengths. Here, the wavelength means the wavelength at which the index of refraction (or refractive index) is to be determined, and being optically flat means that the surface roughness is at least one order of magnitude smaller than the wavelength. There is no constraint on the composition of candidate materials or the optical penetration depth, so small dimension materials may comprise a wide variety of materials; these include single crystals (isotropic or anisotropic), thin films, particles, and so on. Many material systems fall into this category, these include three-dimensional single crystals (with any crystal structures), thin films (physically or chemically grown), two-dimensional organic-inorganic hybrid perovskites (2DHPs), two-dimensional transition metal chalcogenides, superatomic solids, and so on. Described herein are specific embodiments that demonstrate the technique with two-dimensional organic-inorganic hybrid perovskites (2DHPs). The 2DHPs may comprise inorganic perovskite layers (such as made of lead iodide octahedra) and an organic spacer material. The organic material may be a cation spacer that forms ionic bonds with the perovskite layers, for example but not limited to BA (butylamine), BZA (benzylammonium), HA (histammonium), G (guanidinium) and 3AMP (3-(aminomethyl)piperidinium).

The methods described herein for determining refractive index are suitable for absorbing media (e.g., in the above bandgap region of a semiconductor) and can be applied to the emerging and wide-ranging super-molecular single crystals and exfoliated 2D-TMDs, with achievable sizes typically below tens of microns.

Figure 1B:
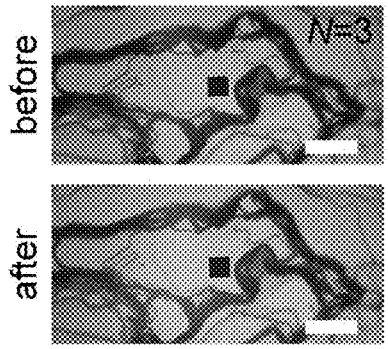
Figure 1C:
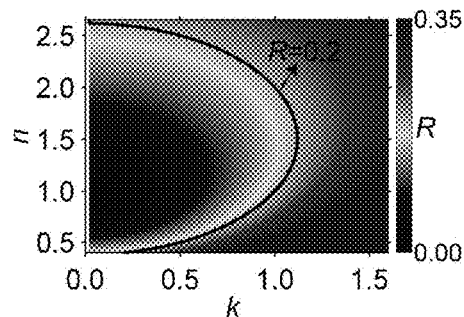

For illustrative purposes, 2DHPs are described regarding experiments and theoretical models. The macroscopic crystals of 2DHPs examined here comprise chemical compositions of $(BA)_2(MA)_{N-1}Pb_NI_{3N+1}$, where N=1~4, BA=$CH_3(CH_2)_3NH_3^+$ and MA=$CH_3NH_3^+$ (FIG. 1A). Although orthorhombic, these materials can be well approximated as uniaxial crystals with the optic axis pointing along $\vec{c}$, due to the negligibly different (<1%) lattice constants along $\vec{a}$ and $\vec{b}$. The ε tensor is written as $$\begin{pmatrix} \varepsilon_{xx} & 0 & 0 \\ 0 & \varepsilon_{yy} & 0 \\ 0 & 0 & \varepsilon_{zz} \end{pmatrix}$$

where $\varepsilon_{xx}=\varepsilon_{yy}\neq\varepsilon_{zz}$, and x, y and z are defined to be parallel to the $\vec{a}$, $\vec{b}$ and $\vec{c}$ axes (FIG. 1A). Previous studies on the refractive index (RI) of 2DHPs were limited to polycrystalline thin films. Because the primary surfaces of 2DHP single crystal flakes, which are parallel to the ab-plane, are only microscopically smooth (FIG. 1B), well-established techniques (e.g., spectroscopic ellipsometry) have been problematic. Although microscopic reflection measurements at normal incidence can be performed for locally smooth regions, the reflectivity (R) of an absorbing medium, with a thickness that significantly exceeds (by a few times) the optical penetration depth depends (only) on both real (n) and imaginary part (k) of RI (FIG. 1C shows the calculated R as a function of n and k using transfer matrix code). Here, the optical penetration depth refers to the depth that light can penetrate into the material. When the material's thickness is less than the optical penetration depth (i.e., if there is finite transmission of light through the material), then as long as the thickness of the material can be determined, the reflection from the material still only depends on n and k, and hence the method demonstrated here can be similarly applied to weakly optically absorbing materials, as well as optically transparent materials.

Figure 1D:
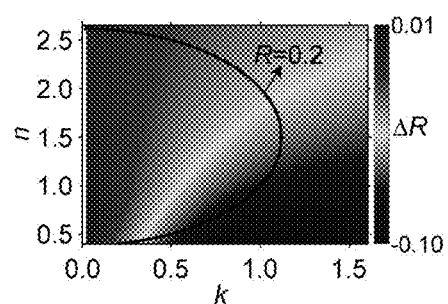

While this presents a problem, one embodiment solves this problem by performing reflection measurements on small-dimension material before and after coating a thin dielectric layer on top of it. For a strongly optically absorbing medium (such as the above bandgap range of direct-bandgap semiconductors), an ultrathin (<<λ/4 where λ is the wavelength) dielectric coating on the absorbing medium produces non-trivial phase shift at the interface, and with it a large change in R (denoted as ΔR). It is preferably that the dielectric coating has a smaller optical absorption coefficient than the material whose refractive index is to be determined. In one embodiment, a separate non-coated sample is measured. In another embodiment, the same sample is measured before coating then measured after coating. In yet another embodiment, a sample is only coated partially so a coated and uncoated portion with measurements taken from both areas. FIG. 1D illustrates the calculated dependence of ΔR on the substrate n and k, due to coating of an ultrathin dielectric layer with known RI and thickness using a transfer matrix calculation. Because points on the contour in FIG. 1C (with constant R) exhibit different ΔR in FIG. 1D, n and k can be determined at each wavelength by solving an inverse problem using R and ΔR as input parameters.

The reflection measurements can be performed with a customized microscope with a white light source (the spectral range of the light source can be ultraviolet, visible, near-infrared, mid-infrared, and beyond) or a laser source, provided that the objective and other components of the microscope are compatible with the spectral coverage of the light source. Commercial microscopes can also be used; the present results were obtained using a Filmetrics F40 microscopic reflectometer. The detailed procedure in extracting the correct n and k from the measured R and ΔR for a particular wavelength is the following. (1) In the two-dimensional data (R as a function of n and k), identify the pair of n and k values, that will yield calculated R that matches the experimental value. (2) Among the identified pairs of n and k values from step (1), find those that will give the calculated ΔR value that matches the experimental counterpart. Because the dielectric coating has different refractive index than the underlying material, a unique solution can be found, as illustrated in FIGS. 1C and 1D.

In one embodiment, to determine the refractive index for materials that have weak optical absorption coefficient, such as the below bandgap range for a direct-bandgap semiconductor or a dielectric material (not to be confused with the dielectric coating), the above technique can still be employed; however, in these cases, the material thickness needs to be determined such that the only unknowns in predicting its reflection before and after the dielectric coating are n and k of the material. Best sensitivity of the method can be obtained by choosing a dielectric coating that has the most different n and k values than the n and k values to be determined, and the thickness of the dielectric coating should be adjusted (for example, by trial and error) to yield ΔR to be on the same order of magnitude as R.

However, while providing small-dimension material with a coating of dielectric could provide beneficial insight, the coating of a dielectric layer on 2DHPs is non-trivial. FIGS. 5A-B illustrate that sputtering of $Al_2O_3$ leads to surface damage because 2DHPs are particularly delicate materials. Thus, the impact of the coating process must be considered, although sputtering (and other deposition techniques such as pulsed-laser deposition or metal-organic chemical vapor deposition) has been demonstrated to be compatible with a wide class of materials. In one embodiment, the dielectric coating is applied by thermal evaporation as a minimally energetic process. Other low-energetic deposition techniques that can be employed include atomic layer deposition, provided that the material is stable under the deposition temperature. In the illustrative embodiment using 2DHPs, the process employed thermal evaporation to coat thin layers of $MoO_x$ with a low melting point. The dielectric material should be one that has known and/or readily quantifiable properties, notably thickness and refractive index. In addition, the dielectric material should be less optically absorbing than the material whose index of refraction is to be determined.

Figure 1E:
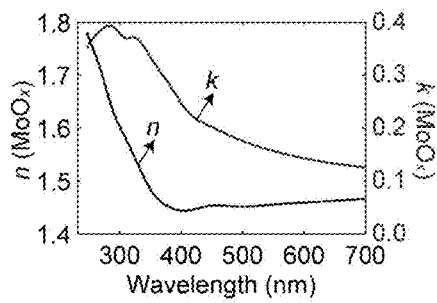
Figure 1F:
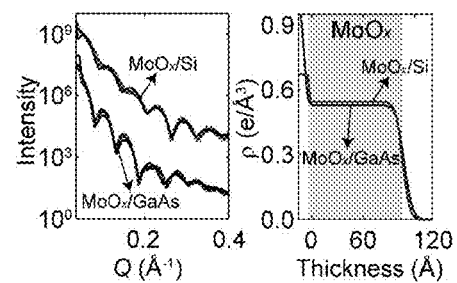
Figure 2A:
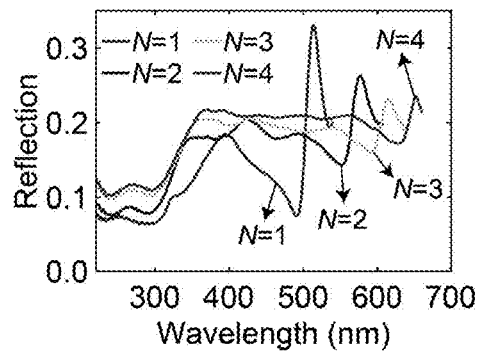
FIGS. 2A-F show determined in-plane optical properties of 2DHPs.
Figure 2B:
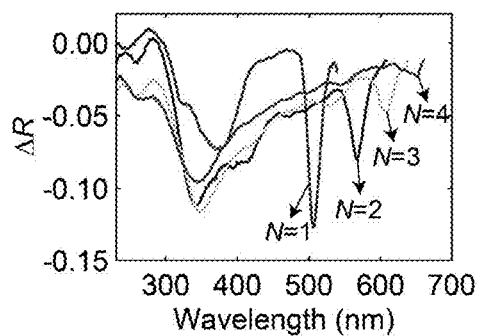
Figure 2C:
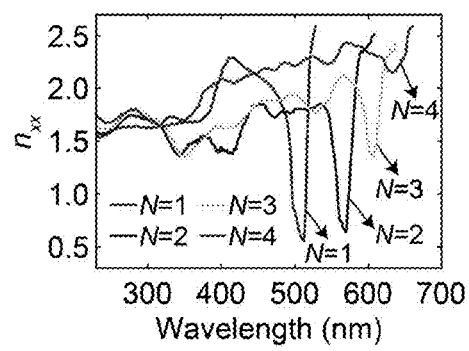
Figure 6A:
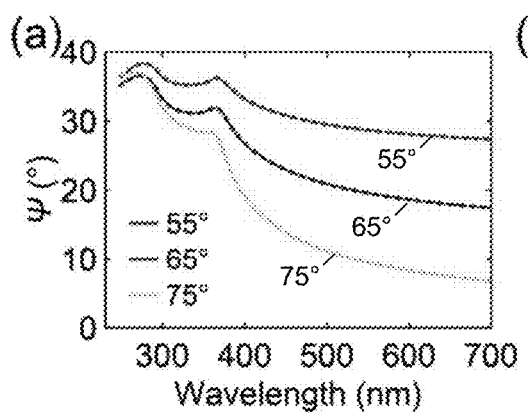
FIG. 6A shows ψ values for $MoO_x$ film on a witness Si wafer obtained from variable angular ellipsometric experiments.
Figure 6B:
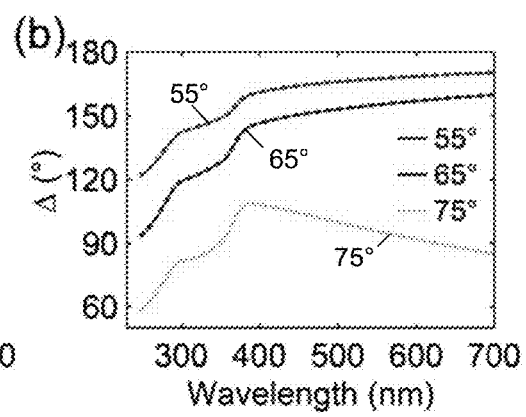
FIG. 6B shows Δ values for $MoO_x$ film on a witness Si wafer obtained from variable angular ellipsometric experiments. The mean-squared-error for the fitting using CompleteEase (J. A. Woolam) was below 1.
Figure 7A:
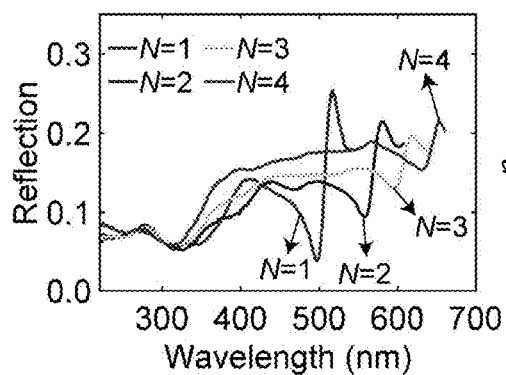
FIG. 7A shows reflectivity from the ab-plane of 2DHPs (N=1~4) after the coating of ~11 nm $MoO_x$.
Figure 7B:
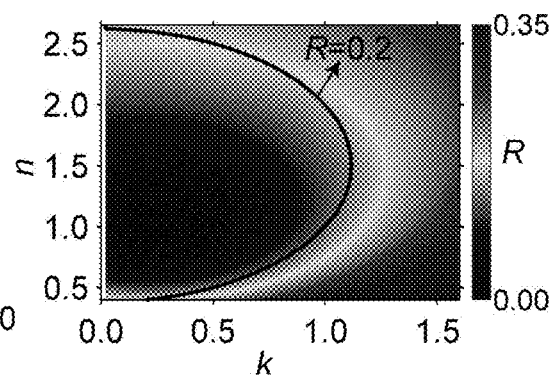
FIG. 7B shows the calculated reflectivity as a function n and k of an absorbing medium, following the coating of ~11 nm $MoO_x$.
Figure 8A:
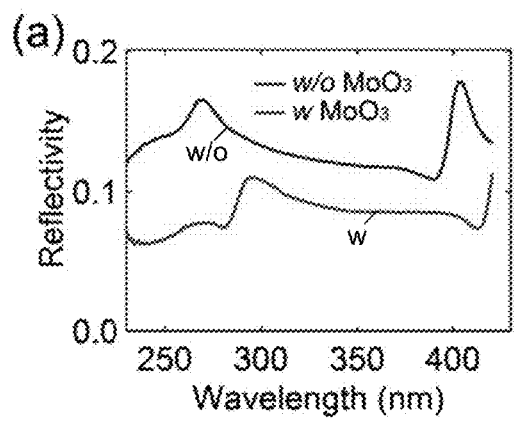
FIG. 8A shows reflectivity from $MAPbCl_3$ single crystal before and after the coating of 11-nm thick $MoO_x$.
Figure 8B:
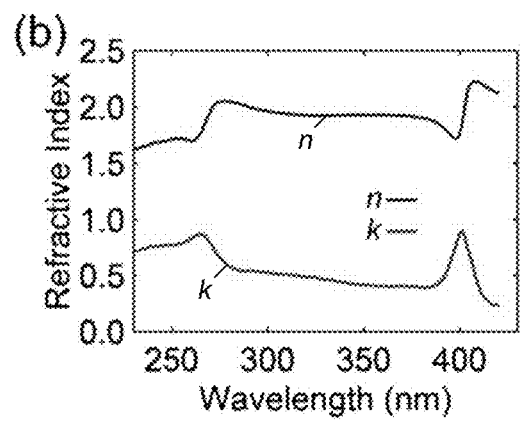
FIG. 8B shows n and k for $MAPbCl_3$.
Figure 8C:
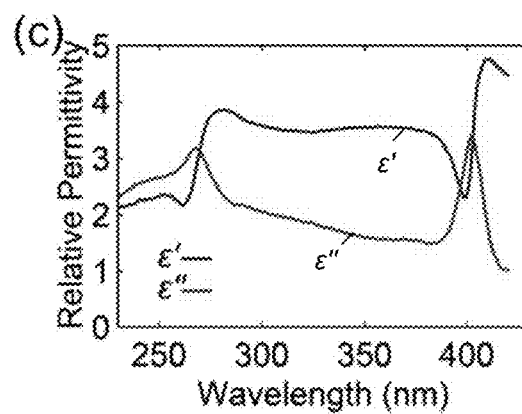
FIG. 8C shows $\epsilon'$ and $\epsilon''$ for $MAPbCl_3$.
Figure 8D:
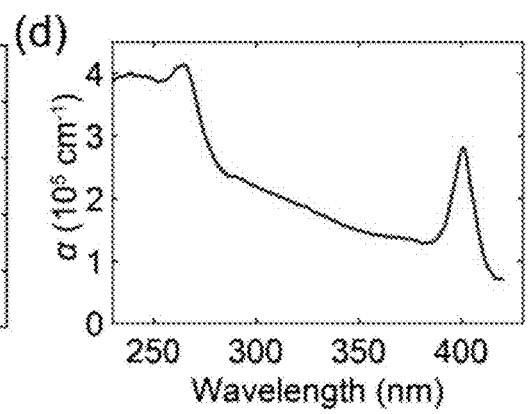
FIG. 8D shows α for $MAPbCl_3$. Data shown in FIGS. 8B-D were determined from reflectivity results shown in FIG. 8A.
Figure 9A:
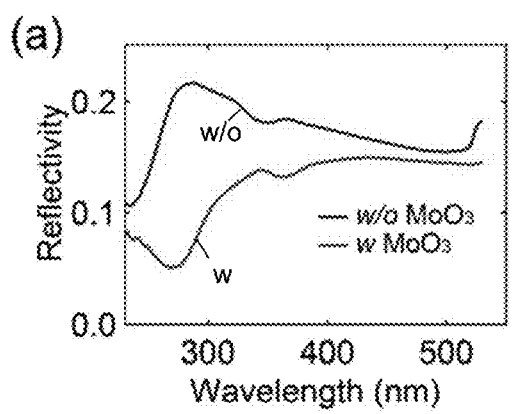
FIG. 9A shows reflectivity from $MAPbBr_3$ single crystal before and after the coating of 11-nm thick $MoO_x$.
Figure 9B:
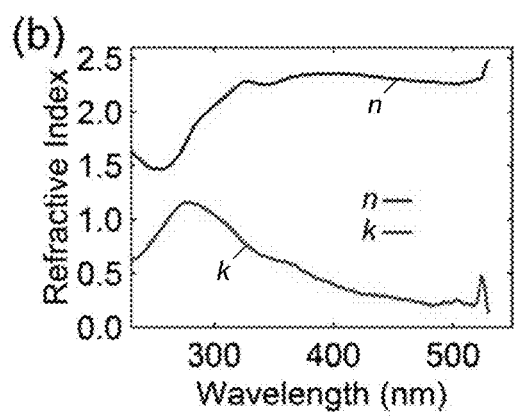
FIG. 9B shows n and k for $MAPbBr_3$.
Figure 9C:
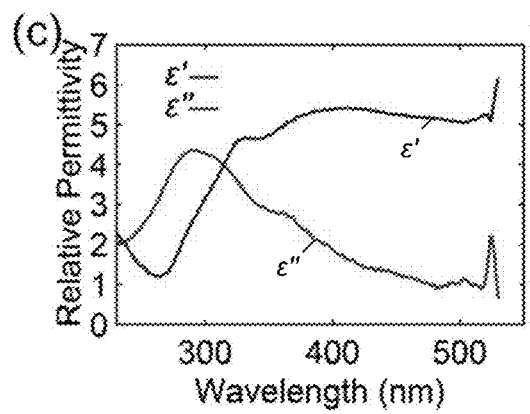
FIG. 9C shows $\epsilon'$ and $\epsilon''$ for $MAPbBr_3$.
Figure 9D:
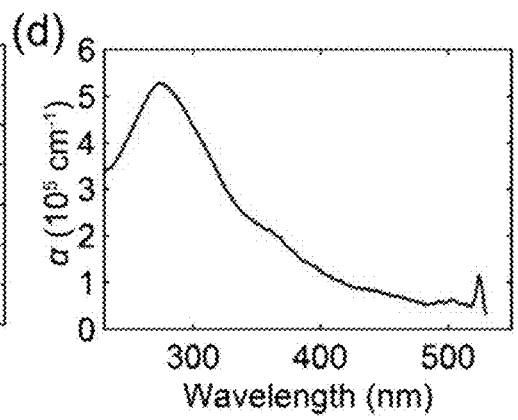
FIG. 9D shows α for $MAPbBr_3$. Data shown in FIGS. 9B-D were determined from reflectivity results shown in FIG. 9A.
Figure 10A:
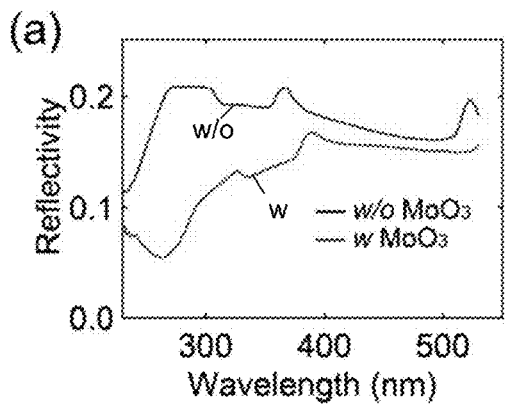
FIG. 10A shows reflectivity from $CsPbBr_3$ single crystal before and after the coating of 11 nm thick $MoO_x$.
Figure 10B:
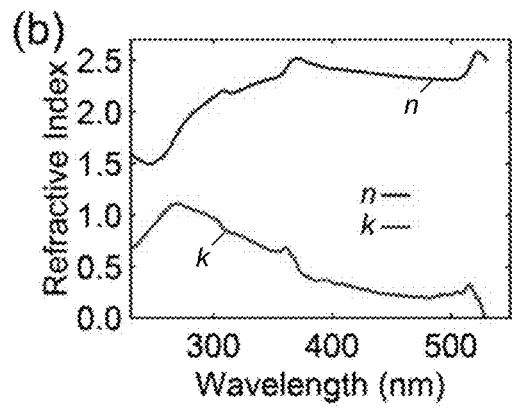
FIG. 10B shows n and k for $CsPbBr_3$.
Figure 10C:
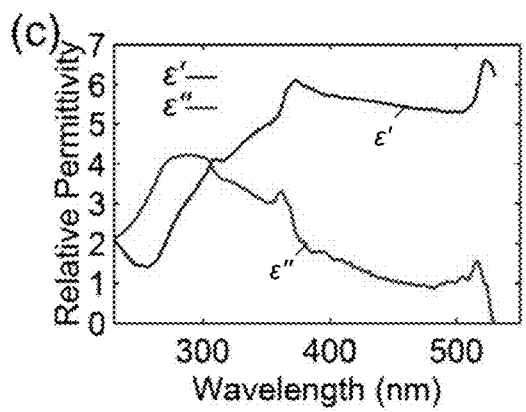
FIG. 10C show $\epsilon'$ and $\epsilon''$ for $CsPbBr_3$.
Figure 10D:
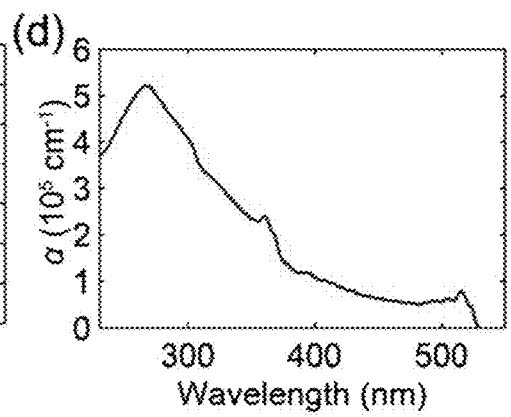
FIG. 10D shows α for $CsPbBr_3$. Data shown in FIGS. 10B-D were determined from reflectivity results shown in FIG. 10A.

The thickness and the refractive index of the dielectric coating were extracted from X-ray reflectivity measurements and ellipsometric measurements, respectively. Other thickness determination methods include cross-sectional transmission or scanning electron microscopy. Thickness can also be known using a quartz crystal microbalance (well-calibrated for the dielectric coating material). The refractive index of certain well-known dielectric materials may also be found in standard references. Referring again to the illustrative embodiment, thickness and RI (FIG. 1E) of the $MoO_x$ films, which showed negligible substrate dependence (FIG. 1F), were extracted from X-ray reflectivity (FIG. 1F) and ellipsometric measurements (FIGS. 6A-B). FIGS. 2A and 2B present R for N=1~4 and ΔR (calculated from R after the coating as plotted in FIGS. 7A-B) following an 11 nm coating of $MoO_x$, for incident light pointing along $\vec{c}$. The determined n and k for N=1~4 along the ab-plane are plotted in FIGS. 2C and 2D, respectively. In addition, n and k were calculated for $MAPbCl_3$, $MAPbBr_3$ and $CsPbBr_3$ (FIGS. 8A-D, 9A-D, and 10A-D) using the same method, and the results agree well with an earlier report.

For 2DHPs, the strength of the excitonic resonance, manifested as a dip in n and a peak in k, strongly increases with decreasing N. It was found that lower members (N=1~2) exhibit some of the strongest dispersions from exciton resonances among known materials, which can be useful for control of the group velocity of light.

Figure 2D:
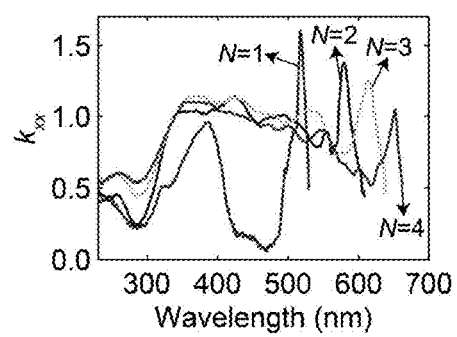
Figure 2E:
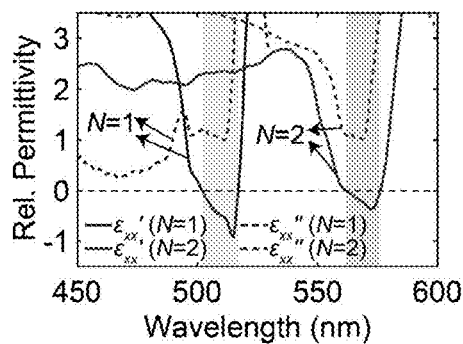
Figure 2F:
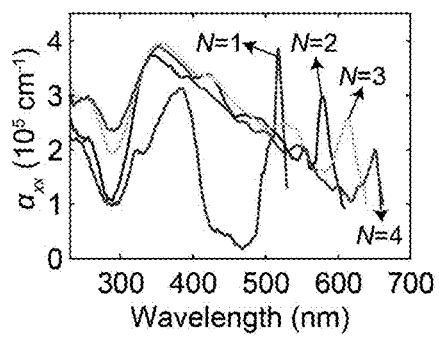
Figure 11A:
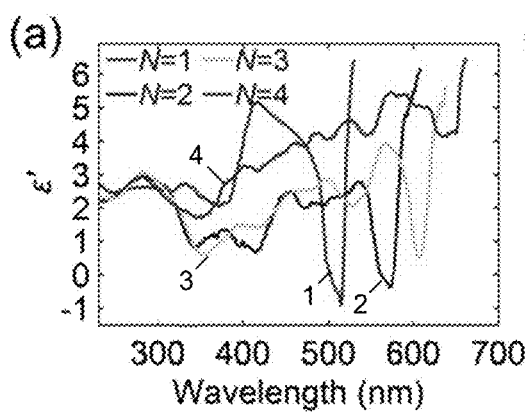
FIG. 11A shows $\epsilon'$ values for 2DHPs (N=1 to 4) along the in-plane direction.
Figure 11B:
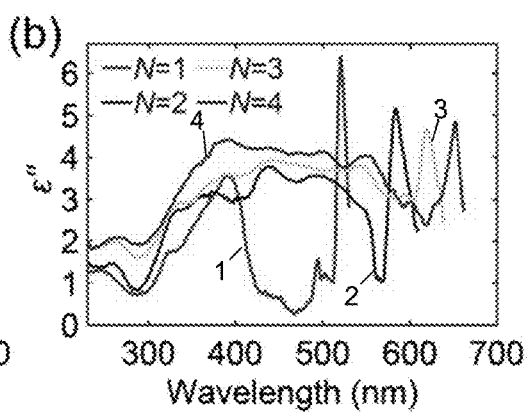
FIG. 11B shows $\epsilon''$ values for 2DHPs (N=1 to 4) along the in-plane direction.
Figure 12A:
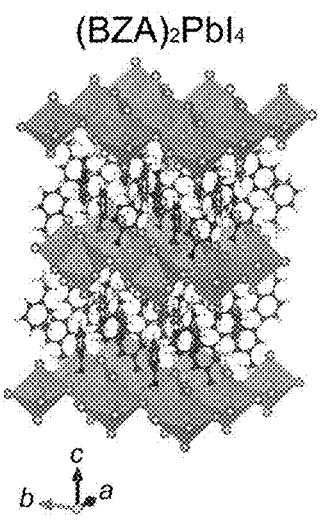
FIGS. 12A-D show crystal structures of 2DHPs comprising of perovskite monolayers separated by different organic spacers.
Figure 12B:
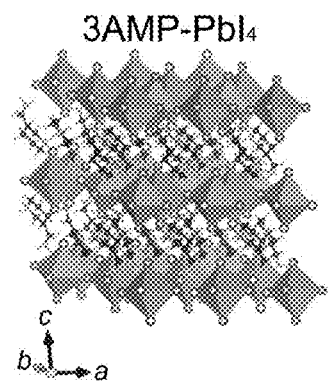
Figure 12C:
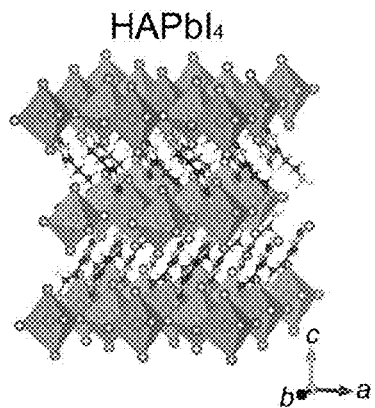
Figure 12D:
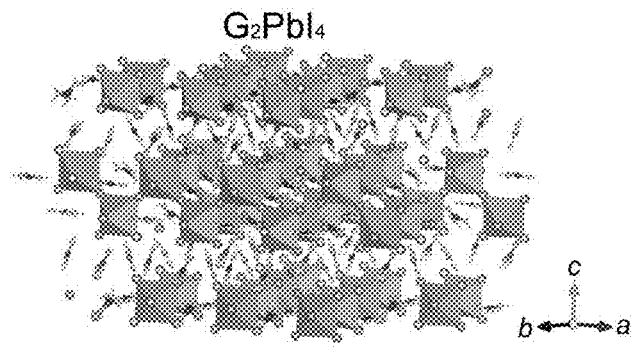
Figure 13A:
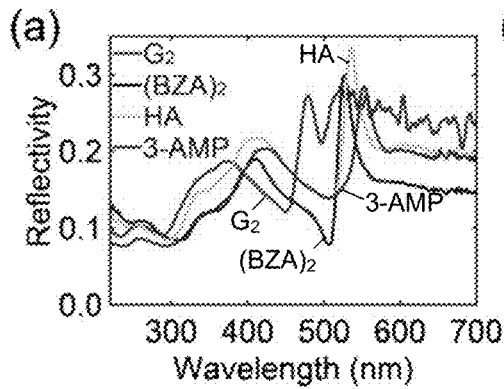
FIG. 13A shows reflectivity from the ab-plane of pristine 2DHPs composed of monolayers of perovskites separated by different organic spacers (G: guanidinium; HA: histaminium; BZA: benzylammonium; 3-AMP: 3-(aminomethyl)piperidinium).
Figure 13B:
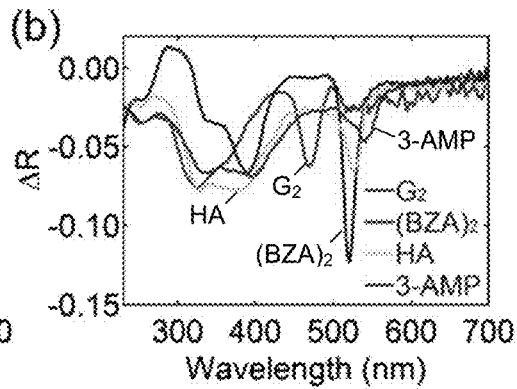
FIG. 13B shows the change of reflectivity following the coating of 11 nm thick $MoO_x$.
Figure 14A:
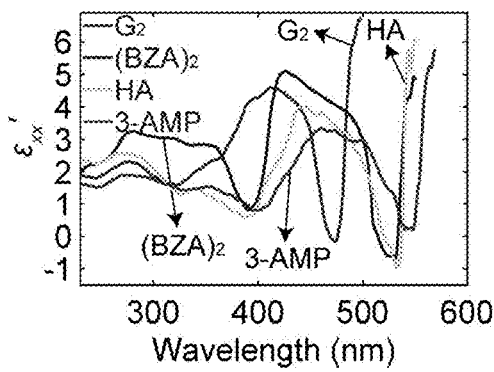
FIGS. 14A-D show optical properties of 2DHPs composed of monolayers of perovskites separated by different organic spacers. All results are for the in-plane directions.
Figure 14B:
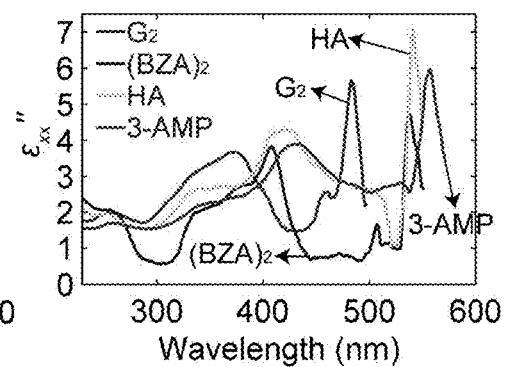
Figure 14C:
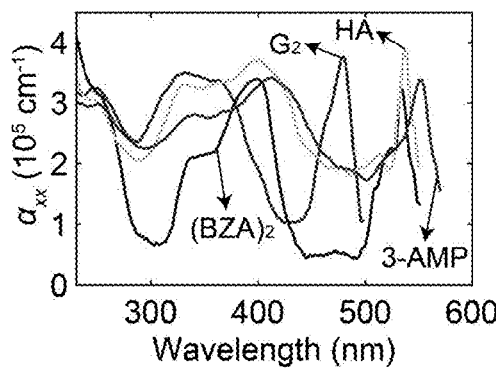
Figure 14D:
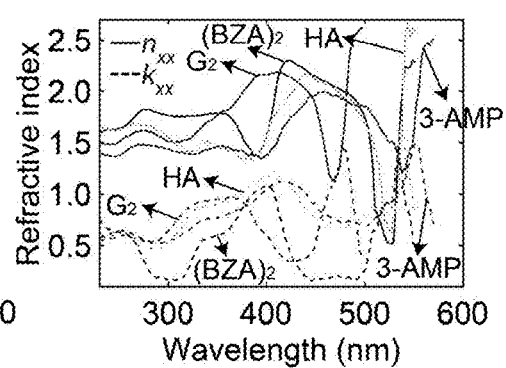

FIGS. 2E and 2F present the real ($\varepsilon'$) and imaginary part ($\varepsilon'$) of relative permittivity for N=1~2 (results for other members are shown in FIGS. 11A-11B), and the absorption coefficient, a, for N=1~4, which were calculated as $\varepsilon'=n^2-k^2$, $\varepsilon''=2nk$, and $\alpha=2\pi\varepsilon''/(n\lambda)$, respectively. FIGS. 2E, 2F, 11A and 11B, which show $\varepsilon'$ and $\varepsilon''$, were based on the data of n and k shown in FIGS. 2C and 2D. Notably, both N=1 and N=2 exhibit negative $\varepsilon'$ at the spectral regime where k>n, with $|\varepsilon'''|$ and $|\varepsilon'|$ having comparable magnitudes. The negative $\varepsilon'$ relates to strong in-plane excitonic polarization that is opposite (out-of-phase) with the driving field. For N=3-4, $\varepsilon'$ remains positive and approaches the behavior of $MAPbI_3$ crystals. The peak a values for N=1~2 range from 3 to 4×10⁵ $cm^{-1}$, which is comparable to 2D transition metal dichalcogenides (TMDs). In contrast to two-dimensional TMDs, which are direct-bandgap only in the monolayer limit, high α and negative $\varepsilon'$ in 2DHPs are bulk properties. Here, "bulk" means that the materials' thickness is much thicker than monolayer (i.e., changing the thickness does not alter the optical property of the material).

The organic cations of 2DHPs occupying the interlayer space offers an effective tuning knob of the exciton binding energy and dielectric confinement, and with them a change of the optical properties (i.e., refractive index) of the materials. FIGS. 3A-B show the resulting n and k values for 2DHPs with different organic spacers, including BZA (benzylammonium), HA (histammonium), G (guanidinium) and 3AMP (3-(aminomethyl)piperidinium). All compositions have monolayer perovskite thickness. Related crystal structures, reflectivity spectra and permittivities are shown in FIG. 12, FIGS. 13A-B, and FIGS. 14A-D. Both $(BZA)_2PbI_4$ and $(HA)PbI_4$ exhibit negative in-plane $\varepsilon'$ with similar amplitude as $(BA)_2PbI_4$ (N=1). In contrast, $G_2PbI_4$ has negative $\varepsilon'$ with reduced magnitude, due to the corrugated perovskite structure that disrupts the strong coupling of light with in-plane excitons. The $\varepsilon'$ of $3AMP-PbI_4$ stays above zero, due to a short lattice constant along $\vec{c}$ and with it a weaker dielectric confinement that, also yields a reduced exciton binding energy manifested as a redshifted absorption peak.

Figure 15A:
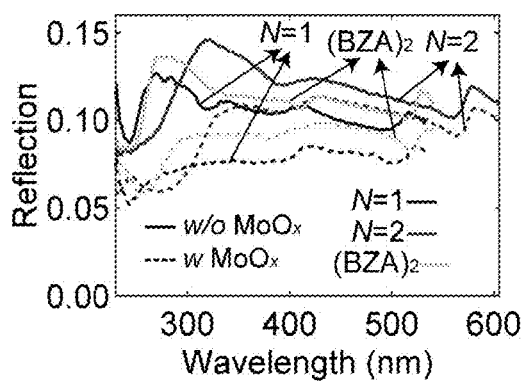
FIGS. 15A-D show optical properties of N=1, N=2 and $(BZA)_2PbI_4$ along the out-of-plane (z) direction.
Figure 15B:
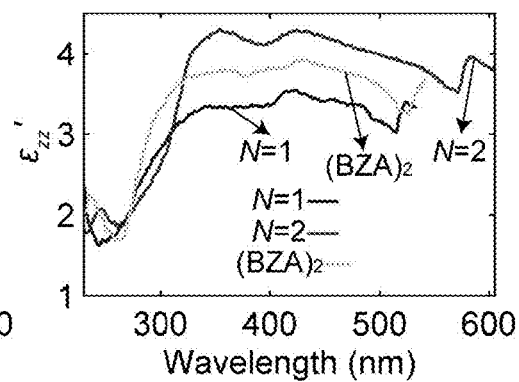
Figure 15C:
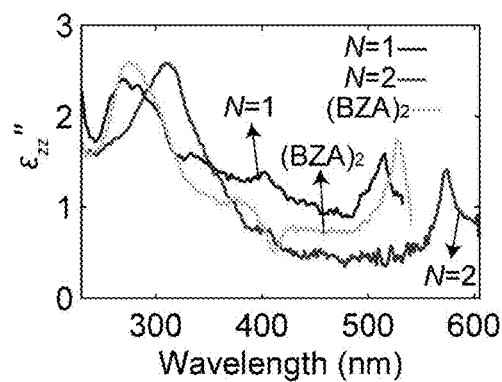
Figure 15D:
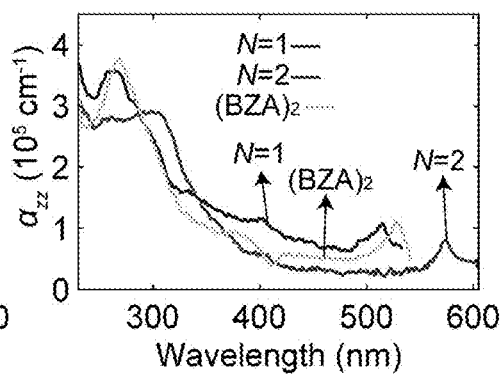
Figure 16A:
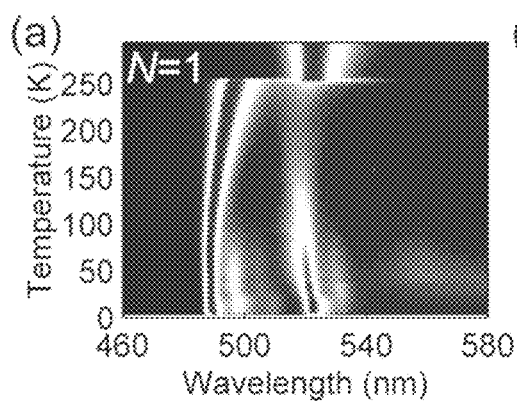
FIGS. 16A-D show temperature dependent photoluminescence color maps for N=1 (FIG. 16A), N=2 (FIG. 16B), N=3 (FIG. 16C) and N=4 (FIG. 16D).
Figure 16B:
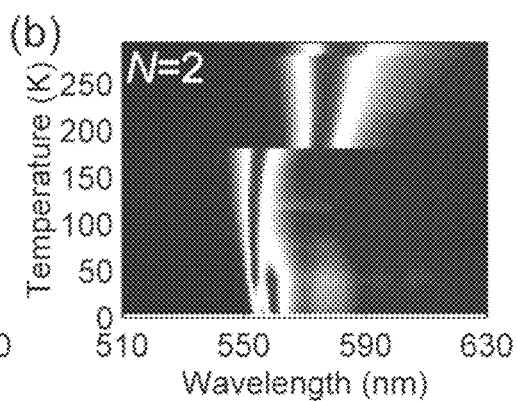
Figure 16C:
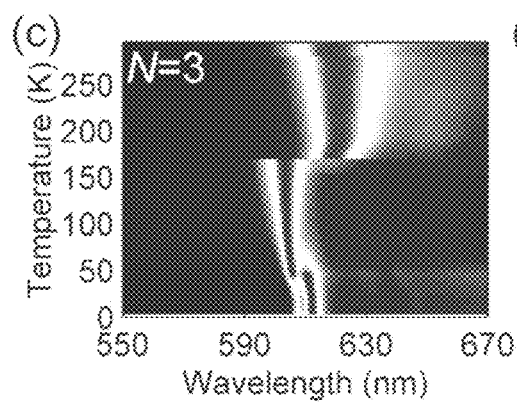
Figure 16D:
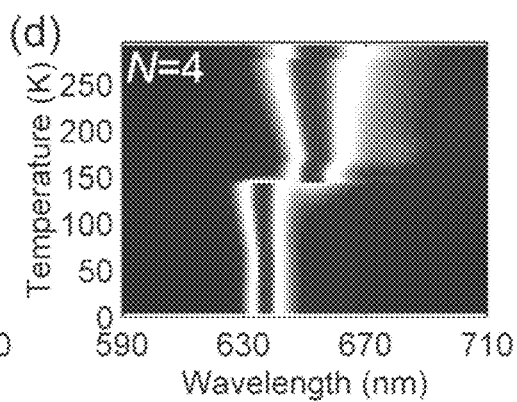

To probe the out-of-plane permittivity ($\varepsilon_{zz}$), reflectivity was measured from the ac-plane with the incident light propagating along $\vec{b}$ and polarized along $\vec{c}$ (FIG. 3C inset). The reflectivity from the ac-plane with polarization along $\vec{a}$ yields the same result as that measured from the ab-plane with un-polarized light, as expected for a uniaxial medium. Note the reflectivity curves (FIG. 15A) do not manifest strong excitonic features when compared with those measured from the ab-plane, and the determined n and k (FIG. 3C), and permittivities (FIGS. 15B-D), show substantially weaker dispersion near the exciton resonance.

Near the exciton transition, $\varepsilon_{xx}=\varepsilon_{yy}<0$ and $\varepsilon_{zz}>0$ for N=1~2 (FIG. 2E) as well as for $(BZA)_2PbI_4$ and $(HA)PbI_4$ (FIGS. 14A-D). Such behavior, by definition, results in a natural type-II hyperbolic dispersion for transverse-magnetic (TM) waves. FIG. 3D displays the TM iso-frequency surfaces for N=1 calculated from the dispersion relation $$\frac{k_x^2}{\varepsilon_{zz}} + \frac{k_z^2}{\varepsilon_{xx}} = \frac{w^2}{c^2}$$

The surface has an ellipsoidal shape at 400 nm where N=1 is normally uniaxial, and turns into a hyperboloid at 513 nm (the negative peak of $\varepsilon'_{xx}$). In both cases the shapes are perturbed by optical losses. The simulated near-field at 513 nm (FIG. 3D inset, left), produced by an embedded dipole emitter, exhibits a resonance-cone-like profile, with enhanced field strength compared to the 400-nm case (FIG. 3D inset, right).

Type-II hyperbolic metamaterials composed of metal-dielectric multilayers were shown to enhance the radiative decay rates of nearby quantum emitters. Here, the highly anisotropic excitonic transitions in 2DHPs produce photonic environments that can inherently facilitate the radiative decay of excitons in the media. This effect was evaluated by calculating the Purcell factors for 2D and 3D perovskites with finite-element simulations. As shown in FIG. 3E, 2DHPs exhibit Purcell factors an order-of-magnitude higher in the hyperbolic regime, compared to $MAPbBr_3$ and $MAPbCl_3$ at their band-edge emission wavelengths. Since the spatial extent of the emitting dipoles (i.e., the size of the excitons) and the spatial dispersion (i.e., nonlocal effects) imposed by the finite size of unit cells (i.e., there is an upper limit on the accessible high wavevectors) were not considered, it is believed that these Purcell-factor estimates represent overestimations. Regardless, relative comparisons between 2D and 3D perovskites indicate that 2DHPs are, among other reasons (such as tightly bound excitons in 2DHPs versus free carriers in 3DHPs), more suitable than their 3D counterparts for light-emitting applications.

The hyperbolic regimes for N=1 and 2 (FIG. 2E) are centered at 513 nm and 571 nm, respectively, which are on the blue edge of their photoluminescence (PL) spectra measured from the primary surfaces (i.e., ab-plane), in which case both the excitation photons and PL photons are polarized in-plane (FIG. 3F). This arises because the out-of-phase condition of the excitonic response relative to the driving electric field takes place on the blue side of the resonance, as predicted by a Lorentzian-type oscillator model. However, the PL spectra measured from the ac-plane (FIG. 3F) show different center wavelengths that depend on the polarization of either the excitation ($E_{exe}$) or emission ($E_{PL}$), and blueshifts along the line of ($E_{exc} \| \vec{c}$)&($E_{PL} \| \vec{a}$), to ($E_{exc} \| \vec{a}$)&($E_{PL} \| \vec{a}$), and to ($E_{exc} \| \vec{a}$)&($E_{PL} \| \vec{c}$). This effect, which is more significant for lower members, arises from the anisotropy in k (FIGS. 2D and 3C) and the Stokes shift between the absorption and emission spectra. In going from ($E_{exc} \| \vec{c}$) to ($E_{exc} \| \vec{a}$), the penetration depth of the excitation light decreases, leading to a reduced re-absorption of the emitted light. From ($E_{PL} \| \vec{a}$) to ($E_{PL} \| \vec{c}$), the self-absorption of PL photons also decreases. Indeed, the high α dictates that emitted photons in the hyperbolic region are strongly recycled (self-absorbed), and for this reason, do not necessarily lead to a reduced PL lifetime. However, the hyperbolic regime should present a better spectral matching with PL photons inside the material (before any re-absorption events occur), and can suppress other non-radiative decay channels such as carrier trapping.

At room temperature, homogeneous broadening due to electron-phonon interactions determines the linewidth and magnitude of exciton resonances in 2DHPs and hence the achievable negativity of the in-plane ε'. To explore excitonic linewidths and enhanced negative ε', performed measurements at lower temperatures. As shown in FIG. 4A, the peak reflectivities for N=1 and 2 reach ~0.6 at ~80K, comparable in magnitude to the recently reported atomically thin mirrors based on $MoSe_2$. For N=3 and 4, peak reflectivities above 0.37 can be obtained, which are higher than the room-temperature value of N=1 and suggest that negative in-plane ε' can be obtained with high members of 2DHPs at low temperatures. A nearly four-fold reduction in the full-width-half-maximum of the PL spectra for all the members (FIGS. 4B, 4D and 15A-D) implies a similarly narrowed exciton resonance linewidth, with significantly larger amplitude of the negative in-plane ε' and lower ε", under the reasonable assumption that the exciton oscillator strength does not vary strongly with temperature. Structural phase transitions, manifested as abrupt blueshifts of both the resonances in the reflectivity curves and the PL spectra (FIG. 4C), were observed for all the members. Determination of temperature dependent optical constants was not attempted due to the phase transitions, which caused morphological changes of the single crystals. However, such studies may be possible by measuring the reflectivity from exfoliated 2DHPs onto two different substrates, and solving an inverse problem based on the reflectivities.

Our work sheds light on how crystal orientations may influence the optical absorption and emission of thin-film photovoltaic and light-emitting devices with 2DHPs as the active layer. We expect that exciton-induced in-plane negative ε' can exist in a variety of material systems including colloidal nanoplatelets, highly ordered organic semiconductors, two-dimensional transition metal dichalcogenides (e.g., $ReS_2$), two-dimensional organic-inorganic hybrid perovskite, and two-dimensional group IV monochalcogenides, wherein excitons are preserved in the bulk. Thus, in various embodiments, the developed refractive index characterization technique can be applied to these materials classes. For materials that have thickness several times larger than the optical penetration depth (as similar to the case of 2DHPs), the procedure described herein can be directly applied. For materials whose thickness is on the same order of the optical penetration depth, the thickness of the materials needs to be determined by other imaging techniques (such as cross-sectional scanning electron microscopy), in order to construct FIG. 1C and FIG. 1D. For artificial metamaterials, the metallic and dielectric components are individually adjustable to achieve spectral and amplitude tuning of the negative ε'. Such feature can be obtained in 2DHPs with (partial) substitution of the metallic cation (from Pb to Sn), the halide anion (from I to Br or Cl), or the organic spacers, at even smaller length scales. The exciton-induced extreme optical anisotropy can be further conceived for polarization conversion, reduced reflection, and strong coupling of excitons with optical cavities through the support of surface modes.

Experimental and Analytical Processes

The experiments described above and the analytical processes referred to above were performed using the techniques and parameters described below.

Synthesis of 2D Hybrid Perovskite Single Crystals.

The synthesis of $(C_3N_2H_4CH_2CH_2NH_3)PbI_4$ (or $HAPbI_4$) and $(C_6H_5CH_2NH_3)_2PbI_4$ (or $(BZA)_2PbI_4$) followed previous report. The synthesis of BA based 2DHPs (N=1 to 4) followed a separate report. The purity and orientation of the single crystals was confirmed by powder X-ray diffraction as well as single crystal θ-2θ X-ray diffraction (Bruker D8 Discover).

For the synthesis of 3AMP-PbI$_4$, an amount of 111.5 mg (0.5 mmol) 99.9% PbO powder was dissolved in 3 ml of hydroiodic acid and 0.5 ml hypophosphorous acid solution by heating under stirring for 5 minutes at 160° C. until the solution turned to clear bright yellow. 0.5 ml hydroiodic acid was added to 57 mg (0.5 mmol) 3AMP in a separate vial under stirring. The protonated 3AMP solution was slowly added into the previous solution while hot. Red plate-like crystals precipitate during slow cooling to room temperature, with a yield of 152 mg (36.6% based on total Pb content).

Synthesis of 3D Perovskite Single Crystals

The preparation of $MAPbBr_3$ single crystals followed the experimental procedure reported in literature. The growth of $MAPbCl_3$ single crystals followed the method reported in literature with modifications. Specifically, equimolar of $CH_3NH_3Cl$ and $PbCl_2$ were first dissolved in 1:1 volumetric ratios of DMF/DMSO to form 1M solution. The mixture solution was heated to 60° C. on a hot plate to initiate crystallization. After 1-2 hours, seed crystals (~1 mm size) were selected and taken out of precursor solution. Meanwhile, saturated mother liquors were prepared by dissolving 3 mmol of $CH_3NH_3Cl$ and $PbCl_2$ in 1 mL of DMSO under rigorous stirring overnight. Saturated liquors were then obtained by filtering the solutions with syringe filter (Millipore, 0.2 μm pore size). Seed crystals were then loaded into filtered liquor solutions for continuous growth at room temperature. After a week, crystals in the size of 3 mm by 3 mm were formed, taken out of solution, and followed by washing with toluene and air drying. CsPbBr$_3$ single crystals were prepared via antisolvent vapor-assisted crystallization, by following the procedure reported in literature.

Thermal Evaporation of MoO$_x$

MoO$_x$ layer was deposited by thermal evaporation of MoO$_3$ (99.99%, Sigma-Aldrich) under a pressure of $8\times10^{-6}$ Torr at a rate of ~0.1 Å/s. Cooling water was utilized to maintain a substrate temperature of ~25° C. during the deposition. The perovskite flakes were attached to Si wafers via carbon tapes. Si and/or GaAs witness wafers were placed adjacent to the perovskite samples. Note that the stoichiometry of thermally evaporated molybdenum oxide is dependent on the pressure, deposition rate and evaporation temperature, hence we use MoO$_x$, rather than MoO$_3$, to represent the evaporated film here.

Optical Characterization

Specular reflection spectra were acquired with Filmetrics F40 microscope (15× objective). For each composition, reflection results were averaged over more than 20 spots, and we found <5% spot-to-spot variations. For reflection measurements on the cross-section (ac-plane) of the single crystal flakes, a wire-grid polarizer was used to control the polarization of the incident beam. For low temperature reflection measurements, samples were placed in a liquid-nitrogen cooled cryostat. Room temperature photoluminescence spectra were collected using a customized microscope with 440 nm excitation produced from a Fianium supercontinuum laser source with a spot size of several μm. Temperature dependent photoluminescence spectra were measured with 400 nm excitation, produced by second harmonic generation of an Ti:sapphire amplifier output with a spot size of ~1 mm, and the samples were mounted in a 4K closed-cycle cryostat. Ellipsometric measurements of the MoO$_x$/Si samples were performed with a J.A. Woollam M2000U system.

Reflection Calculation, and Optical Simulation

A customized transfer-matrix code was used to calculate the reflection of pristine as well as MoO$_x$ coated 2DHPs, at both normal and oblique incidences. The Purcell factor was calculated from finite-element simulations (COMSOL Multiphysics). In the 3D simulations, a point dipole (oriented either parallel or perpendicular to the optic axis) was placed inside the anisotropic medium. Integration of the Poynting vector was performed over a spherical surface centered at the dipole with a radius of 10 nm.

X-Ray Reflectivity

The X-ray reflectivity measurements were conducted on a 9 kW Rigaku SmartLab Workstation. Highly collimated incident X-ray beam (flux: ~$10^9$ cps, slits: 0.1 mm by 5 mm) were generated from a Cu rotating anode and projected onto the sample surfaces. The X-ray reflectivity measurements employed the Bragg-Brentano geometry, and the collected data and subsequent electron density modeling were processed using Igor-based Motofit packages. The reflected intensity is plotted as a function of momentum transfer, $Q=4\pi\cdot\sin(2\theta)/\lambda$, where $2\theta$ is the scattering angle and $\lambda$ is the wavelength (1.542 Å). The origin of the electron density profile (FIG. 1F, right) is set as the film/substrate interface.

Definitions

As used herein, the singular forms "a", "an," and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes, and omissions may also be made in the design, operating conditions, and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method of determining a refractive index of a two-dimensional organic-inorganic hybrid perovskite comprising:

selecting a dielectric material with a known refractive index;

depositing a coating of the dielectric material on a first sample of the two-dimensional organic-inorganic hybrid perovskite, forming a coated sample having a thickness;

engaging the coated sample with a laser of an optical testing device, the laser having a wavelength and a thickness of the coating being no more than ¼ of the wavelength;

determining a reflectivity of the coated sample;

determining a reflectivity of an uncoated sample of the two-dimensional organic-inorganic hybrid perovskite;

determining a change in reflectivity (ΔR) by comparing the reflectivity of the coated sample and the reflectivity of the uncoated sample; and determining the refractive index of the two-dimensional organic-inorganic hybrid perovskite at the wavelength based upon ΔR and the reflectivity of the uncoated sample.

2. The method of claim 1, wherein the two-dimensional organic-inorganic hybrid perovskite is optically flat.

3. The method of claim 1, wherein the coating is applied to only a portion of the two-dimensional organic-inorganic hybrid perovskite.

4. The method of claim 1, wherein the coated sample and the second uncoated sample are a contiguous structure.

5. The method of claim 1, wherein the coated sample and the uncoated sample are non-contiguous structures and the uncoated sample has a second thickness that is greater than an optical penetration depth of the laser at the wavelength wherein the method further comprises engaging with the optical testing device the uncoated sample.

6. The method of claim 1, wherein the depositing of the coating of the coated sample is by thermal evaporation or atomic layer deposition.

7. The method of claim 1, wherein the coating of dielectric material is less optically absorbing than the two-dimensional organic-inorganic hybrid perovskite.

8. The method of claim 1, wherein the coated sample of the two-dimensional organic-inorganic hybrid perovskite has a thickness that is greater than an optical penetration depth of the laser at the wavelength.

9. The method of claim 1, wherein the coated sample of the two-dimensional organic-inorganic hybrid perovskite has a thickness within an order of magnitude of an optical penetration depth of the laser at the wavelength, the method further comprising determining the thickness of the coated sample.

10. The method of claim 1, wherein determining the refractive index comprises: 1) identifying, from the determined reflectivity of the coated sample, pairs of n and k values; 2) from the identified pairs of n and k values, determining a unique pair that yields a calculated ΔR value that matches a determined change in reflectivity; and 3) determining the refractive index of the uncoated sample by identifying the unique pair of n and k.

11. A method of determining a refractive index of a small dimension material comprising:

selecting a dielectric material with a known refractive index;

depositing a coating of the dielectric material on a the small-dimension material so that a portion of the small dimension material is coated with the dielectric material and a second portion of the small dimension material is uncoated by the dielectric material;

engaging the portion of the small dimension material coated with the dielectric material with a laser of an optical testing device, the laser having a wavelength and a thickness of the coating being no more than ¼ of the wavelength;

determining a reflectivity of the portion of the small dimension material;

determining a reflectivity of the second portion of the small dimension material;

determining a change in reflectivity (ΔR) representing a phase shift exhibited by a comparison of a reflectivity of the portion of the small-dimension material and a reflectivity of the second portion of the small-dimension material; and determining the refractive index of the second portion of the small-dimension material at the wavelength based upon ΔR and the reflectivity of the second portion of the small-dimension material.

12. The method of claim 11, wherein the small dimension material is selected from a group consisting of colloidal nanoplatelets, highly ordered organic semiconductors, two-dimensional transition metal dichalcogenides, two-dimensional organic-inorganic hybrid perovskite, and two-dimensional group IV monochalcogenides.

13. The method of claim 11, wherein the portion of the small-dimension material and the second portion of the small-dimension material are a contiguous structure.

14. The method of claim 11, wherein the portion of the small-dimension material and the second portion of the small-dimension material are non-contiguous structures and the second portion of the small-dimension material has a second thickness that is greater than an optical penetration depth of the laser at the wavelength wherein the method further comprises engaging with the optical testing device the second portion of the small-dimension material.

15. The method of claim 11, wherein the depositing of the coating of the portion of the small-dimension material is by thermal evaporation or atomic layer deposition.

16. The method of claim 11, wherein the coating of dielectric material is less optically absorbing than the small dimension material.

17. The method of claim 11, wherein the first portion of the small dimension material has a thickness that is greater than an optical penetration depth of the laser at the wavelength.

18. The method of claim 11, wherein the portion of the small dimension material has a thickness within an order of magnitude of an optical penetration depth of the laser at the wavelength, the method further comprising determining the thickness of the portion of the small-dimension material.

19. The method of claim 11, wherein determining the refractive index comprises: 1) identifying, from the determined reflectivity of the portion of the small-dimension material, pairs of n and k values; 2) from the identified pairs of n and k values, determining the unique pair that yields a calculated ΔR value that matches a determined change in reflectivity; and 3) determining the refractive index of the second portion of the small-dimension material by adding the unique pair of n and k.

* * * * *